US005728543A

United States Patent [19]
Dörschug et al.

[11] Patent Number: 5,728,543
[45] Date of Patent: Mar. 17, 1998

[54] CLOSTRIPAIN CATALYZED HYDROLYSIS OF PREPROINSULIN ANALOGS INTO CORRESPONDING INSULINS

[75] Inventors: Michael Dörschug, Bochum; Klaus-Peter Koller, Bad Soden am Taunus; Rüdiger Marquardt, Frankfurt am Main; Johannes Meiwes, Hofheim am Taunus, all of Germany

[73] Assignee: Hoechst Aktiengesellschaft, Frankfurt am Main, Germany

[21] Appl. No.: 291,060

[22] Filed: Aug. 8, 1994

Related U.S. Application Data

[63] Continuation of Ser. No. 155,912, Nov. 23, 1993, abandoned, which is a continuation of Ser. No. 754,001, Sep. 3, 1991, abandoned.

[30] Foreign Application Priority Data

Sep. 5, 1990 [DE] Germany ............... 40 28 118.3

[51] Int. Cl.$^6$ ............... C12P 21/06; C12N 9/52; A61K 38/28
[52] U.S. Cl. ............... 435/68.1; 435/220; 530/303
[58] Field of Search ............... 435/68.1, 220; 530/303

[56] References Cited

U.S. PATENT DOCUMENTS

| | | | |
|---|---|---|---|
| 4,639,333 | 1/1987 | Obermeier et al. | 530/303 |
| 4,644,057 | 2/1987 | Bicker et al. | 530/409 |

FOREIGN PATENT DOCUMENTS

| | | |
|---|---|---|
| B-89007 | 9/1983 | European Pat. Off. |
| 0158981 | 10/1985 | European Pat. Off. |
| 0195691 | 9/1986 | European Pat. Off. |
| 0264250 | 3/1988 | European Pat. Off. |
| A-347781 | 12/1989 | European Pat. Off. |
| A-367163 | 5/1990 | European Pat. Off. |
| 3440988 | 7/1986 | Germany. |
| 3919852 | 12/1989 | Germany. |
| 4012818.0 | 10/1991 | Germany. |

OTHER PUBLICATIONS

Thim et al. (1982) *Biochim. Biophys. Acta, 703(2)*, 131–141.
Thim et al., The Primary Structure of Porcine Glicentin (Proglucagon), Reg. Peptides 2 (2):139–150 (1981).

Stryer (1981) "Biochemistry", 2nd Ed., pp. 847–849, Freeman JG., San Francisco.

Fletterick et al. (1985) "Molecular Structure, Macromolecules in Three Dimensions," pp. 121–139, Blackwell Scientific, Oxford.

Groo et al. (1960) *Bull. Soc. Chim. Biol., 42*, 559–568, see also *Chem. Abst., 55*, Abst # 5615 i (for applicants convenience).

Thim et al. (1981) *Peptides, 2, Supp 2*, 37–39.

Yagisawa et al., High–Efficiency Transpeptidation Catalysed by Clostripain and Electrostatic Effects in Substrate Specificity, Mar. 15, 1990, The Biochemical Journal pp. 771–775.

Deber et al., Enzymatic Synthesis of Arginine Proline Peptide Bonds Using Clostripain as a Catalyst, 1985 Proceedings of the American Peptide Symposium, pp. 355–358.

Roth et al., Preferential Degradation of the I Subunit of Purified Insulin Receptor, Dec. 10, 1983, The Journal of Biological Chemistry pp. 14456–14460.

Burgess, production of Human Calcitonin (hCT) in E. Coli, 1987 Proceedings of the CETUS–UCLA Symposium on Protein, vol. 68, pp. 435–442.

Kemmler et al., "Studies on the Conversion of Proinsulin to Insulin, I. Conversion in Vitro in Trypsin and Carboxypeptidase B", J. Biol. Chem., Chem. vol. 246 No. 22, pp. 6786–6791 (1971).

Mitchell et al., "Purification and Properties of Clostridiopeptidase B (Clostripain)", J. Biol. Chem., vol. 213, No. 18, pp. 4683–4692 (1968).

Labouesse, "L'Hydrolyse Du Glucagon Par La Clostripaine", Bull. Soc. Chim. Biol., vol. 42, No. 11, pp. 1293–1304 (1960).

*Primary Examiner*—Jon P. Weber
*Attorney, Agent, or Firm*—Finnegan, Henderson, Farabow, Garrett & Dunner, L.L.P.

[57] ABSTRACT

A process is described to specifically hydrolyze the amino acid chain of preproinsulin analogs to give the corresponding insulins. The hydrolysis is catalyzed by clostripain and, if necessary, carboxypeptidase B.

14 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 87 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Xaa Xaa Xaa Xaa Xaa Xaa Xaa Xaa Xaa Xaa Xaa Xaa Xaa Xaa Xaa Xaa
 1               5                  10                  15
Xaa Xaa Xaa Xaa Xaa Xaa Xaa Xaa Xaa Xaa Xaa Xaa Xaa Xaa Xaa Arg
                20                  25                  30
Arg Xaa Xaa Xaa Xaa Xaa Xaa Xaa Xaa Xaa Xaa Xaa Xaa Xaa Xaa Xaa
        35                  40                  45
Xaa Xaa Xaa Xaa Xaa Xaa Xaa Xaa Xaa Xaa Xaa Xaa Xaa Xaa Xaa Xaa
    50                  55                  60
Lys Arg Xaa Xaa Xaa Xaa Xaa Xaa Xaa Xaa Xaa Xaa Xaa Xaa Xaa Xaa
 65                         70                  75              80
Xaa Xaa Xaa Xaa Xaa Xaa Xaa
                85
```

( 2 ) INFORMATION FOR SEQ ID NO:2:

( i ) SEQUENCE CHARACTERISTICS:
        ( A ) LENGTH: 137 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..31

( D ) OTHER INFORMATION: /note="All or some of residues may be missing."

( i x ) FEATURE:
    ( A ) NAME/KEY: Peptide
    ( B ) LOCATION: 127
    ( D ) OTHER INFORMATION: /note="If hydroxy substituted, peptide terminates with this residue."

( i x ) FEATURE:
    ( A ) NAME/KEY: Peptide
    ( B ) LOCATION: 128..137
    ( D ) OTHER INFORMATION: /note="If present, may be missing nine amino acids."

( x i ) SEQUENCE DESCRIPTION: SEQ ID NO:2:

```
Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa Val
            20                  25                  30

Xaa Xaa Xaa Xaa Cys Xaa Xaa Xaa Xaa Xaa Xaa Xaa Xaa Xaa Xaa Xaa
        35                  40                  45

Cys Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                   80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Gly Xaa Xaa Xaa Xaa Cys Cys
            100                 105                 110

Xaa Xaa Xaa Xaa Cys Xaa Xaa Xaa Xaa Xaa Xaa Xaa Xaa Cys Xaa Xaa
        115                 120                 125

Xaa Xaa Xaa Xaa Xaa Xaa Xaa Xaa Xaa
     130                 135
```

( 2 ) INFORMATION FOR SEQ ID NO:3:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..30
        ( D ) OTHER INFORMATION: /note="May be cleaved off, or if present, C- terminal must be Arg preceded by 1-29 Xaa's."

( i x ) FEATURE:
        ( A ) NAME/KEY: Peptide
        ( B ) LOCATION: 61..91
        ( D ) OTHER INFORMATION: /note="If Xaa at position 61 is L-arginine, then 62-91 are missing. If not, then 61-91 are the C- chain of human or animal proinsulin."

( i x ) FEATURE:
        ( A ) NAME/KEY: Peptide
        ( B ) LOCATION: 112
        ( D ) OTHER INFORMATION: /note="Xaa is an amino acid from the group comprising Asn, Gln, Asp, Glu, Gly, Ser, Thr, Ala or Met, and if hydroxy substituted, then peptide terminates at this position."

( i x ) FEATURE:
        ( A ) NAME/KEY: Peptide
        ( B ) LOCATION: 113..122
        ( D ) OTHER INFORMATION: /note="If present, up to 8 amino (xi) SEQUENCE DESCRIPTION: SEQ ID NO:3:

| Xaa 1 | Xaa | Xaa | Xaa | Xaa 5 | Xaa | Xaa | Xaa | Xaa | Xaa 10 | Xaa | Xaa | Xaa | Xaa | Xaa 15 |
|---|---|---|---|---|---|---|---|---|---|---|---|---|---|---|
| Xaa | Xaa | Xaa | Xaa 20 | Xaa | Xaa | Xaa | Xaa | Xaa 25 | Xaa | Xaa | Xaa | Xaa | Phe 30 | Val |
| Xaa | Xaa | Xaa 35 | Xaa | Cys | Xaa | Xaa | Xaa 40 | Xaa | Xaa | Xaa | Xaa | Xaa 45 | Xaa | Xaa |
| Cys | Xaa 50 | Xaa | Xaa | Xaa | Xaa | Xaa 55 | Xaa | Xaa | Xaa | Xaa | Xaa 60 | Xaa | Xaa | Xaa |
| Xaa 65 | Xaa | Xaa | Xaa | Xaa | Xaa 70 | Xaa | Xaa | Xaa | Xaa | Xaa 75 | Xaa | Xaa | Xaa | Xaa 80 |
| Xaa | Xaa | Xaa | Xaa | Xaa 85 | Xaa | Xaa | Xaa | Xaa | Xaa 90 | Xaa | Gly | Xaa | Xaa | Xaa 95 |
| Cys | Cys | Xaa | Xaa 100 | Xaa | Cys | Xaa | Xaa | Xaa 105 | Xaa | Xaa | Xaa | Xaa | Xaa 110 | Cys | Xaa |
| Xaa | Xaa | Xaa 115 | Xaa | Xaa | Xaa | Xaa | Xaa 120 | Xaa | Xaa | | | | | |

(2) INFORMATION FOR SEQ ID NO:4:

(i) SEQUENCE CHARACTERISTICS:
    (A) LENGTH: 122 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..30
    (D) OTHER INFORMATION: /note="May be cleaved off, or if present, C- terminal must be Arg preceded by 1-29 Xaa's."

(ix) FEATURE:
    (A) NAME/KEY: Peptide
    (B) LOCATION: 61..91
    (D) OTHER INFORMATION: /note="If Xaa at position 61 is L-arginine, then 62-91 are missing. If not, then 61-91 are the C- chain of human or animal proinsulin."

(ix) FEATURE:
    (A) NAME/KEY: Peptide
    (B) LOCATION: 112
    (D) OTHER INFORMATION: /note="If hydroxy substituted, then peptide terminates at this position."

(ix) FEATURE:
    (A) NAME/KEY: Peptide
    (B) LOCATION: 113..122
    (D) OTHER INFORMATION: /note="If present, up to 8 amino acids may be missing."

(xi) SEQUENCE DESCRIPTION: SEQ ID NO:4:

| Xaa 1 | Xaa | Xaa | Xaa | Xaa 5 | Xaa | Xaa | Xaa | Xaa | Xaa 10 | Xaa | Xaa | Xaa | Xaa | Xaa 15 |
|---|---|---|---|---|---|---|---|---|---|---|---|---|---|---|
| Xaa | Xaa | Xaa | Xaa 20 | Xaa | Xaa | Xaa | Xaa | Xaa 25 | Xaa | Xaa | Xaa | Xaa | Phe 30 | Val |
| Xaa | Xaa | Xaa 35 | Xaa | Cys | Xaa | Xaa | Xaa 40 | Xaa | Xaa | Xaa | Xaa | Xaa 45 | Xaa | Xaa |
| Cys | Xaa 50 | Xaa | Xaa | Xaa | Xaa | Xaa 55 | Xaa | Xaa | Xaa | Xaa | Thr 60 | Xaa | Xaa | Xaa |
| Xaa 65 | Xaa | Xaa | Xaa | Xaa | Xaa 70 | Xaa | Xaa | Xaa | Xaa | Xaa 75 | Xaa | Xaa | Xaa | Xaa 80 |

```
Xaa Xaa Xaa Xaa Xaa Xaa Xaa Xaa Xaa Xaa Xaa Gly Xaa Xaa Xaa Xaa
                85                      90              95

Cys Cys Xaa Xaa Xaa Cys Xaa Xaa Xaa Xaa Xaa Xaa Xaa Xaa Cys Asn
            100             105                 110

Xaa Xaa Xaa Xaa Xaa Xaa Xaa Xaa Xaa Xaa
            115             120
```

( 2 ) INFORMATION FOR SEQ ID NO:5:

( i ) SEQUENCE CHARACTERISTICS:
       ( A ) LENGTH: 66 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:5:

```
Asp Thr Thr Val Ser Glu Pro Asp Pro Asn Ser Asn Gly Arg Phe Val
 1               5                  10                  15

Asn Gln His Leu Cys Gly Ser His Leu Val Glu Ala Leu Tyr Leu Val
            20                  25                  30

Cys Gly Glu Arg Gly Phe Phe Tyr Thr Pro Lys Thr Arg Gly Ile Val
        35                  40                  45

Glu Gln Cys Cys Thr Ser Ile Cys Ser Leu Tyr Gln Leu Glu Asn Tyr
        50                  55                  60

Cys Asn
65
```

CLOSTRIPAIN CATALYZED HYDROLYSIS OF PREPROINSULIN ANALOGS INTO CORRESPONDING INSULINS

This application is a continuation of application Ser. No. 08/155,912, filed Nov. 23, 1993, now abandoned, which is a continuation of Ser. No. 07/754,001, filed Sep. 3, 1991, abandoned.

Insulins are composed of two polypeptide chains, the A chain which contains 21 amino-acid residues, and the B chain with 30 amino-acid residues. The A and B chains are connected together via two disulfide linkages, with the cysteine residues in positions A7 and B7, and A20 and B19, being linked together. There is a third disulfide linkage between A6 and A11. Animal and human insulins are produced in the pancreas in the form of preproinsulins. Human preproinsulin is composed, for example, of a prepeptide with 24 amino-acid residues, to which is attached a proinsulin with 86 amino-acid residues with the following configuration: prepeptide-B-Arg-Arg-C-Lys-Arg-A (SEQ. ID NO: 1), where C is an amino-acid chain with 31 residues. During excretion from the islets of Langerhans, the prepeptide is cleaved off to result in proinsulin. Finally, the C-chain is cleaved proteolytically to result in active human insulin.

Genetic engineering methods are increasingly allowing preproinsulins to be expressed in microorganisms (EP-A-347 781, EP-A-367 163). The prepro sequences are usually cleaved off chemically and/or enzymatically (DE-P-3 440 988, EP-A-0264250). Known enzymatic conversion methods are based on cleavage with trypsin and carboxypeptidase B (Kemmler W. et al. J. Biol. Chem., 246 (1971) 6786–6791; EP-A-195 691; EP-B-89007). The disadvantage of these methods is the formation of large amounts of byproducts, which can be removed from the reaction solution only with difficulty. In the particular case of the conversion of human preproinsulin into human insulin (human insulin, HI) there is formation of large amounts of de-Thr(B30)-human insulin (de-Thr(B30)-HI).

This byproduct differs from HI only by the absence of a terminal amino acid and is very difficult to remove from the reaction solutions.

It is possible to add certain heavy metals, especially nickel, to the cleavage mixture to reduce this byproduct formation (EP-A 0264 250). This way of carrying out the reaction is undesirable from the industrial point of view because of the heavy loading of effluents with heavy metals. Thus there is a need for a preproinsulin conversion of maximum specificity and environmental compatibility.

Clostripain (clostriopeptidase B; EC 3.4.22.8) is an enzyme from the culture filtrate of Clostridium histolyticum with a molecular weight of about 30,000 to 80,000, which has both proteolytic and amidase/esterase activity (Mitchell, W. M., Harrington, W. F., J. of Biol. Chem., 243 (18), 4683–4692, 1968). It is distinguished by a high specificity for Arg-C linkages. Thus, in the isolated B chain of insulin, clostripain cleaves the Arg-Gly linkage 500 times more rapidly than the Lys-Ala linkage and in glucagon only the Arg-Arg, the Arg-Ala and the Lys-Tyr are cleaved. The relative initial rates of hydrolysis of these three bonds are 1,1/7 and 1/300. (Labouesses B., Bull. Soc. Chim. Biol., 42, 1293, 1960). It has now been found, surprisingly, that clostripain brings about specific C-terminal cleavage behind arginine in preproinsulin with negligible cleavage of the amino-acid chain behind the arginine (B22) present in the B chain.

Hence the invention relates to a process for the hydrolysis of the amino-acid chain of preproinsulin of the formula I (SEQ. ID NO: 2)

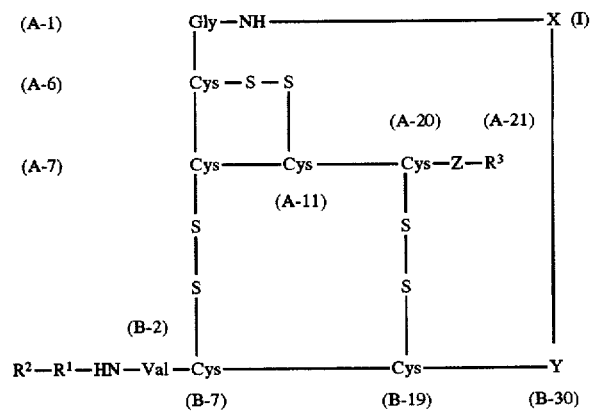

in which

R¹ is n amino acids, where n is the integer 0 or 1,

R² is hydrogen, an amino acid which can be cleaved off chemically or enzymatically, or a peptide with 2 to 30 amino-acid residues, R³ is a hydroxyl group, an amino acid or a peptide with 2 to 10 amino acids, X is L-arginine or a peptide with 2 to 45 amino acids and with a C-terminal and N-terminal L-arginine residue, Y is a genetically encodable amino acid, Z is a genetically encodable amino acid, A1 to A20 or B2 to B29 is an amino-acid sequence, which is natural or has been modified by replacement of one or more amino-acid residues, of human or animal insulins, which comprises the preproinsulin being hydrolyzed in the presence of clostripain and, where appropriate, being converted with carboxypeptidase B into the corresponding insulin.

The amino-acid sequence of peptides and proteins is designated from the N-terminal end of the amino-acid chain. Proteases hydrolyze the peptide linkage between the amino acids of peptides and proteins. Clostripain hydrolyzes L-arginine-containing peptides or proteins specifically behind arginine. The products formed in the hydrolysis reaction on preproinsulins are insulin derivatives or polypeptides which have a C-terminal arginine residue, or amino acids.

Examples of the meaning of the term natural amino acids are Gly, Ala, Ser, Thr, Val, Leu, Ile, Asp, Asn, Glu, Gln, Cys, Met, Tyr, Phe, Pro, Hyp, Trp, Arg, Lys Hyl, Orn, Cit or His.

Examples of the term genetically encodable amino acid are Gly, Ala, Ser, Thr, Val, Leu, Ile, Asp, Ash, Glu, Gln, Cys, Met, Arg, Lys, His, Tyr, Phe, Trp, Pro or seleno-cysteine.

Preferred preproinsulins of the formula I (SEQ. ID NO: 3) are those in which

R¹ is Phe,

R² is hydrogen, a natural amino acid or a peptide with 2 to 30 natural amino acids and with C-terminal L-arginine at the end, R³ is a hydroxyl group, a natural amino acid or a peptide with 2 to 10 natural amino acids, X is L-arginine or a C chain of a human or animal proinsulin, Y is an amino acid from the group comprising Thr, Ala or Ser, Z is an amino acid from the group comprising Asn, Gln, Asp, Glu, Gly, Ser, Thr, Ala or Met, A1 to A20 or B2 to B29 are the amino-acid sequence of human or animal insulins.

Particularly preferred preproinsulins of the formula I (SEQ. ID NO: 4) are those in which $R^1$ is Phe, $R^2$ is hydrogen or a peptide with 2 to 30 natural amino acids and with C-terminal L-arginine at the end, $R^3$ is a hydroxyl group, a natural amino acid or a peptide with 2 to 10 natural amino acids, X is L-arginine or a C chain of human, porcine or bovine proinsulin, Y is Thr, Z is Asn A1 to A20 or B2 to B29 are the amino-acid sequence of human, porcine or bovine insulin.

Especially preferred insulins are those already proposed in German patent applications P 39 19 852 and P 40 12 818.0. For example InsuArg with the following amino-acid sequence (SEQ. ID NO: 5):

NH$_2$-Asp Thr Thr Val Ser Glu Pro Asp Pro Asn Ser Asn Gly Arg Phe Val Asn Gln His Leu Cys Gly Ser His Leu Val Glu Ala Leu Tyr Leu Val Cys Gly Glu Arg Gly Phe Phe Tyr Thr Pro Lys Thr Arg Gly Ile Val Glu Gln Cys Cys Thr Ser Ile Cys Ser Leu Tyr Gln Leu Glu Asn Tyr Cys Asn—COOH.

Clostripain (EC 3.4.22.8) is an extracellular thiol protease from Clostridia. The enzyme is a heterodimer and has no homology whatever with other known thiol proteases. The enzyme has an extremely high specificity for Arg-XXX linkages, especially Arg-Pro. It can be characterized by a molecular weight between 30,000 and 80,000 and an isoelectric point of pH 4.8 to 4.9. Examples of activators are cysteine, mercaptoethanol, dithiothreitol or calcium ions.

Clostripain is inhibited in the presence of, for example, tosyl-L-lysine chloromethyl ketone, hydrogen peroxide, EDTA, $Co^{2+}$, $Cu^{2+}$ or $Cd^{2+}$ ions or citrate.

Clostripain is prepared by fermentation using microorganisms. In this process, Clostridia are cultivated until clostripain accumulates in the nutrient medium. A suitable example is *Clostridium histolyticum*, especially *Clostridium histolyticum* DSM 627. Mutants and variants of the said microorganisms are also suitable as long as they synthesize clostripain.

Culturing is carried out anaerobically, singly or in mixed culture, for example submerged in non-agitated culture in the absence of oxygen or in fermenters, where appropriate with the introduction of nitrogen, inert gases or other gases apart from oxygen. The fermentation is carried out in a temperature range from about 10° to 45° C., preferably about 25° to 40° C., especially 30° to 38° C. Fermentation takes place in a pH range between 5 and 8.5, preferably between 5.5 and 8. Under these conditions, the culture broth generally shows a detectable accumulation of the enzyme after 1 to 3 days. The synthesis of clostripain starts in the late log phase and reaches its maximum in the stationary phase of growth. The production of the enzyme can be followed by means of activity assays (Mitchell W., Meth. of Enzym., vol. 47 (1977), pages 165–170).

The nutrient solution used for producing clostripain contains 0.2 to 6%, preferably 0.5 to 3%, of organic nitrogen compounds, and inorganic salts. Suitable organic nitrogen compounds are: amino acids, peptones, also meat extracts, milled seeds, for example of corn, wheat, beans, soybean or the cotton plant, distillation residues from alcohol production, meat meals or yeast extracts. Examples of inorganic salts which the nutrient solution can contain are chlorides, carbonates, sulfates or phosphates of the alkali metals or alkaline earth metals, iron, zinc and manganese, but also ammonium salts and nitrates.

Although the optimal fermentation conditions differ for each microorganism, they are either already known to the person skilled in the art or easy to establish in preliminary tests. Clostripain can be purified by classical processes, for example by ammonium sulfate precipitation, ion exchange or gel permeation chromatography. The enzyme can be coupled by conventional methods (Colowick and Kaplan, Meth. Enzymol., vol. XLIV).

It is possible to employ for the enzymatic conversion both whole cells in free or immobilized form and the isolated enzyme product, which can likewise be carrier-bound.

The cleavage of the preproinsulins of the formula I with clostripain is carried out in an aqueous medium which can also be mixed with water-miscible organic constituents such as, for example, alcohols, ketones, urea or N,N-dimethylformamide. In particular, it is possible to add to the reaction mixture, to improve pH control during the reaction, appropriate inorganic or organic buffers such as phosphate, tris, glycine, HEPES and the like. The concentration of the preproinsulins during the cleavage is, for example, between 0.01 mg/ml and 100 mg/ml, preferably between 0.1 mg/ml and 10 mg/ml. The ratio of preproinsulin to clostripain is (mg to units (U)) 1:0.01 to 1:1,000, preferably 1:0.1 to 1:50.

The temperature of the reaction can likewise be varied within a wide range. A preferred temperature range is between 0° C. and +80° C., and a temperature between +20° C. and +40° C. is particularly preferred.

The pH of the reaction can vary between pH 4 and pH 12, and the range between pH 6 and pH 9 is particularly preferred.

The time required for the conversion of the preproinsulins into the corresponding intermediates can be varied within wide limits depending on the reaction conditions, for example it can be between 15 min and 48 h, while a reaction time of between 1 h and 6 h is preferred.

The enzyme is activated before use in a suitable manner in the presence of a mercaptan. Mercaptans suitable in principle for this are all compounds which contain SH groups, and DTT, DTE, mercaptoethanol, thioglycolic acid or cysteine is preferably used. The concentration of the mercaptan can be varied within a wide range, with concentrations between 0.1 mM and 100 mM being preferred. The activation buffer also contains $Ca^{2+}$ ions, preferably $CaCl_2$. The activation is carried out between pH 4 and pH 12, preferably between pH 6 and pH 8, and the range pH 7 to pH 8 is particularly preferred. A suitable buffer substance, for example tris, HEPES, glycine and the like, can be added to maintain the pH. The activation temperature can be between 0° C. and 60° C., the range 0° C. to 10° C. being preferred, particularly preferably 0° C. to 5° C. The enzyme activated in this way can either be used directly or, where appropriate, be freed of activation buffer by chromatography on ®Ultrogel AcA 202.

The cleavage, according to the invention, of preproinsulin of the formula I results in insulin derivatives with arginine residues at the C-terminal end of the insulins and the corresponding amino acids and/or peptides which have been cleaved off. The insulin derivatives can, if desired, be converted with carboxy-peptidase B into the corresponding insulins. This can take place in the same reaction mixture at the same time as clostripain or else successively under the above-mentioned reaction conditions, in which case the insulin derivative can be isolated, where appropriate, before the carboxypeptidase B treatment using methods known per se, such as, for example, chromatography or crystallization. Carboxypeptidase B can be employed in dissolved or in immobilized form. The ratio of carboxypeptidase B to insulin derivative is (weight to weight) about 1:10 to 1:5,000, preferably about 1:500 to 1:3,500 and particularly preferably about 1:1,000 to 1:3,000.

The ratio of carboxypeptidase B to clostripain is (weight to weight) about 1:1 to 10:1 and preferably 2:1 to 5:1.

The reaction products of the clostripain and/or carboxypeptidase B cleavage can be, for example, precipitated out by lowering the pH and/or purified using known methods of column chromatography. The resulting insulin can be formulated in conventional presentations and used as pharmaceutical for the treatment of diabetes mellitus.

The process according to the invention is described in detail in the examples which follow. Unless indicated otherwise, percentage data relate to weight.

EXAMPLE 1

Clostridium histolyticum DSM 627 is cultivated in a nutrient solution of the following composition:

| | |
|---|---|
| casein peptone | 3% |
| meat extract | 3% |
| yeast extract | 0.5% |
| cysteine | 0.05% |
| $KH_2PO_4$ | 0.15% |
| pH 7.2 | |

1% inoculation of the preculture is carried out. Cultivation takes place in closed bottles under anaerobic conditions at 37° C. for about 2 days. The microorganism strain is maintained in the abovementioned nutrient solution containing 50% glycerol at −20° C. The fermenter is inoculated with 1% preculture. A fermenter of 10 l capacity and containing 8 l of nutrient solution is inoculated. Cultivation is carried out with nitrogen being passed in at 33° C. and constant pH of 7.0 for 24 h. The measured enzyme activity in the culture filtrate was 20,000 U/l (Mitchell W., Meth. of Enzym., vol. 47, pages. 165–170, 1977).

The working up was carried out by removing the cells by centrifugation at about 6,000 g, sterilization by filtration through a filter with a pore size of 0.22 µm, and addition of 60% ice-cold (−20° C.) methanol to the filtrate. The solution was then maintained at −20° C. for 24 h and subsequently centrifuged (8,000 g). The pellet was dissolved in sterile double-distilled water and centrifuged (12,000 g). The measured enzyme activity in the pellet was 300 U/ml, 200 U/mg of protein. The yield was 75% of the activity measured in the fermenter.

EXAMPLE 2

The cells were cultured as in Example 1. The production medium in the fermenter comprised:

| | |
|---|---|
| Protease peptone (Difco) | 5% |
| Cysteine | 0.05% |
| $KH_2PO_4$ | 0.15% |
| pH 7.2 | | and was inoculated With 2% preculture. The clostripain activity was 45,000 U/ml in the culture filtrate.

The working up was carried out by tangential flow filtration on 0.3 µm membranes (Filtron, Omega membrane) to remove the cells and tangential flow filtration on 10 KD membranes (Flitton, Omega membrane) to concentrate the dissolved clostripain. The concentration factor was 20. The concentrate was then desalted and chromatographed on DEAE-cellulose. Clostripain activity 1,000 U/ml; yield 85%. The enzyme preparation is stored at −20° C. until used.

EXAMPLE 3

A. Activation of clostripain

50 µl of enzyme preparation (200 U/ml, 286 U/mg from Example 1)

1 µl of activation buffer (250 mM DTT, 125 mM $CaCl_2$)

content in the mixture:

| | |
|---|---|
| DTT | 5 mM |
| $CaCl_2$ | 2.5 mM | incubation on ice for 2 h the enzyme is diluted 1:40 with 25 mM tris/HCl buffer pH 7.8 for the cleavage reaction.

B. Clostripain cleavage mixture to liberate (B31) Arg-insulin

100 µl InsuArg (1 mg/ml)
20 µl KCl (1M)
5 µl tris/HCl (1M, pH 7.8)
55 µl $H_2O$
20 µl clostripain (1:40 dilution)
content in the mixture:

| | |
|---|---|
| Insu-Arg | 0.5 mg/ml |
| clostripain | 2.5 U/ml |
| DTT | 12.5 µM |
| tris/HCl | 25 mM |
| KCl | 100 mM |
| $CaCl_2$ | 6 µM | incubation at 28° C. for 1–2 h, the reaction can easily be checked by HPLC, then the reaction stopped with tosyl-L-lysine chloromethyl ketone (TLCK).

reaction stopped by addition of 1 µl of TLCK (15 mM)

storage at 4° C.

result: Human insulin-Arg. No formation of human insulin(deB30) measurable by HPLC.

C. Carboxypeptidase B cleavage mixture for liberating human insulin

200 µl of clostripain cleavage mixture
10 µl of carboxypeptidase B (1:100 dilution)
carboxypeptidase content in the mixture: 2.5 µg/ml
incubation at 28° C. for 2–4 h, the reaction can easily be checked by HPLC
for the reaction, carboxypeptidase B (759 U/ml, 150 U/mg, from porcine pancreas) is diluted 1:1,000 with 25 mM tris/HCl buffer pH 7.8 result: Human insulin. No formation of insulin(deB30) measurable by HPLC.

D. HPLC analysis

The cleavages were checked using an RP 18 column (0.125M $NH_4(SO_4)_2$ adjusted to pH 4 with $H_2SO_4$, 25–50%

EXAMPLE 4

| | |
|---|---|
| Clostripain: | 200 U/ml (from Example 1) |
| Activation buffer: | 500 mM tris/HCl, pH 7.8 |
| | 100 mM DTT |
| | 25 mM CaCl$_2$ |
| Activation: | 100 μl of clostripain solution |
| | 10 μl of activation buffer |
| Folding mixture: | 35.7 mg of human pre-B-chain-A-chain insulin S-sulfonate |
| | 315 μl of 1 M mercaptoethanol |
| | 105 μl of 1 M ascorbic acid |
| | 100 μl of 20 mM glycine buffer, pH 10.7 |

The folding was carried out in a cold room at 4° C. overnight, and the folding yield was 0.152 mg/ml. After removal of impurities by pH precipitation at pH 5.0, tris is added to a final concentration of 50 mM and the pH is adjusted to 7.8 with HCl. 30 μl of enzyme solution were added. Cleavage was carried out at 30° C. and was followed by HPLC.

Result: The abovementioned preproinsulin can be cleaved to human insulin-Arg. The formation of insulin(deB30) is minimal.

---

We claim:

1. A process for the hydrolysis of the amino-acid chain of preproinsulin of the formula I (SEQ. ID NO: 2)

```
(A-1)        Gly—NH————————————————X   (I)
                    |
(A-6)        Cys — S — S
                    |           |
                    |       (A-20)   (A-21)
(A-7)        Cys————Cys—————————Cys—Z—R³
                    |           |
                 (A-11)         |
                    S           S
                    |           |
                    |           |
                    S           S
     (B-2)          |           |
R²—R¹—HN—Val—Cys————————————————Cys—————————Y
              (B-7)         (B-19)       (B-30)
``` in which $R^1$ is n amino acids, where n is the integer 0 or 1, $R^2$ is hydrogen, an amino acid which can be cleaved off chemically or enzymatically, or a peptide with 2 to 30 amino-acid residues, $R^3$ is a hydroxyl group, an amino acid or a peptide with 2 to 10 amino acids, X is L-arginine or a peptide with 2 to 45 amino acids and with a C-terminal and N-terminal L-arginine residue, Y is a genetically encodable amino acid, Z is a genetically encodable amino acid, A1 to A20 or B2 to B29 is an amino-acid sequence, which is natural or has been modified by replacement of one or more amino-acid residues, of human or animal insulins, which comprises the preproinsulin being hydrolyzed by clostripain and, where appropriate, being converted with carboxypeptidase B into the corresponding insulin, and recovering said corresponding insulin.

2. The process as claimed in claim 1, in which is used the preproinsulin of the formula I (SEQ ID NO: 3) in which $R^1$ is Phe, $R^2$ is hydrogen, a natural amino acid or a peptide with 2 to 30 natural amino acids and with C-terminal L-arginine at the end, $R^3$ is a hydroxyl group, a natural amino acid or a peptide with 2 to 10 natural amino acids, X is L-arginine or a C chain of a human or animal pro-insulin, Y is an amino acid from the group consisting of Thr, Ala and Ser, Z is an amino acid from the group consisting of Asn, Gln, Asp, Glu, Gly, Ser, Thr, Ala and Met, A1 to A20 or B2 to B29 are the amino-acid sequence of human or animal insulins.

3. The process as claimed in claim 2, in which is used the preproinsulin of the formula I (SEQ ID NO: 4) in which $R^1$ is Phe, $R^2$ is hydrogen or a peptide with 2 to 30 natural amino acids and with C-terminal L-arginine at the end, $R^3$ is a hydroxyl group, a natural amino acid or a peptide with 2 to 10 natural amino acids, X is L-arginine or a C chain of human, porcine or bovine proinsulin, Y is Thr, Z is Asn A1 to A20 or B2 to B29 are the amino-acid sequence of human, porcine or bovine insulin.

4. The process as claimed in claim 1, which is carried out at a pH between 4 and 12.

5. The process as claimed in claim 4, which is carried out at a pH between 6 and 9.

6. The process as claimed in claim 1, wherein the concentration of the preproinsulins of the formula I (SEQ ID NO: 2) is between 0.01 mg/ml and 100 mg/ml.

7. The process as claimed in claim 6, wherein the concentration of the preproinsulins of the formula I (SEQ ID NO: 2) is between 0.1 mg/ml and 10 mg/ml.

8. The process as claimed an claim 1, wherein the preproinsulin/clostripain ratio (mg to units) is 1:0.01 to 1:1,000.

9. The process as claimed in claim 8, wherein the preproinsulin/clostripain ratio (mg to units) is 1:0.1 to 1:50.

10. The process as claimed in claim 1, wherein the reaction temperature is between 0° C. and +80° C.

11. The process as claimed in claim 10, wherein the reaction temperature is between +20° C. and +40° C.

12. The process as claimed in claim 1, wherein carboxypeptidase B is present at the same time or is employed after cleavage with clostripain.

13. The process as claimed in claim 1, wherein clostripain, carboxypeptidase B or clostripain and carboxypeptidase B are present in immobilized form.

14. The process as claimed in claim 1, in which is used the preproinsulin of the formula I (SEQ. ID NO: 4) in which $R^1$ is Phe, $R^2$ is hydrogen or a peptide with 2 to 30 natural amino acids and with C-terminal L-arginine, $R^3$ is a hydroxyl group, a natural amino acid or a peptide with 2 to 10 natural amino acids, X is L-arginine or a C chain of human, porcine or bovine proinsulin, Y is Thr, Z is Asn A1 to A20 or B2 to B29 are the amino-acid sequence of human, porcine or bovine insulin.

* * * * *